US00PP23325P2

(12) United States Plant Patent
Brazelton et al.

(10) Patent No.: US PP23,325 P2
(45) Date of Patent: Jan. 15, 2013

(54) BLUEBERRY PLANT NAMED 'ZF06-043'

(50) Latin Name: *Vaccinium corymbosum*
Varietal Denomination: ZF06-043

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 13/200,000

(22) Filed: Sep. 14, 2011

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

PP19,381 P2 10/2008 Lyrene

*Primary Examiner* — Annette Para
(74) *Attorney, Agent, or Firm* — Davis Wright Tremaine LLP; Dale C. Hunt; Wenhua Yu

(57) ABSTRACT

The new blueberry plant variety 'ZF06-043' is provided. 'ZF06-043' is an ornamental variety intended for nursery, landscape, and home garden use. The new variety has deep green foliage with pink and orange new growth, which turns a deep purple color in the fall, retaining its foliage throughout the winter. 'ZF06-043' has a round, compact growth habit. The new variety ripens in mid-July and produces mildly sweet, firm berries in moderately loose clusters. The plant is moderately vigorous, with an estimated chilling requirement of 500 hours.

5 Drawing Sheets

Latin name of the family, genus, and species: Family—Ericaceae. Genus—*Vaccinium*. Species—*corymbosum*.

Variety denomination: The new blueberry plant claimed is of the variety denominated 'ZF06-043'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry hybrid known as a *Vaccinium corymbosum* hybrid and referred to as 'ZF06-043', as herein described and illustrated.

The new blueberry plant variety 'ZF06-043' was selected in Lowell, Oreg., in 2006. 'ZF06-043' is an ornamental variety intended for nursery, landscape, and home garden use. The new variety has deep green foliage with pink and orange new growth, which turns a deep purple color in the fall, retaining its foliage throughout the winter. 'ZF06-043' has a round, compact growth habit. The new variety ripens in mid-July and produces mildly sweet, firm berries in moderately loose clusters. The plant is moderately vigorous, with an estimated chilling requirement of 500 hours.

The new blueberry plant originated from a cross of 'Toro' (pollen parent, unpatented) by 'FLX-2' (female parent, U.S. Plant Pat. No. 19,381). The female parent was produced by a cross between 'FL92-9' (unpatented) and 'Sunshineblue' (unpatented). The pollen parent was produced by a cross between 'Earliblue' (unpatented) and 'Ivanhoe' (unpatented). The new blueberry plant variety 'ZF06-043' has been planted in replicated trials since 2007.

The new variety differs from the patented female parent 'FLX-2' in that 'ZF06-043' is smaller in size and has more pronounced orange and pink leaf color.

The new variety differs from the unpatented pollen parent 'Toro' in that 'ZF06-043' is smaller in size, has smaller leaves, and has pronounced orange and pink leaf color.

The new blueberry plant variety 'ZF06-043' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'ZF06-043' has not been observed under all possible environmental conditions. The phenotype may vary somewhat with variations in environment and cultural practices, such as temperature and light intensity, without any variance in genotype.

The following traits have been repeatedly observed in Lowell, Oreg., and are determined to be the unique characteristics of the new blueberry plant variety 'ZF06-043':

1. Deep green foliage with pink and orange new growth;
2. Deep purple fall foliage;
3. Foliage remains on the plant throughout the winter;
4. Compact growth habit.

BRIEF DESCRIPTION OF THE DRAWINGS

The accompanying photographic illustrations show, in full color, typical specimens of the foliage and fruit of the new variety 'ZF06-043'. The colors are as nearly true as is reasonably possible in a color representation of this type.

BOTANICAL DESCRIPTION

Figure 1:
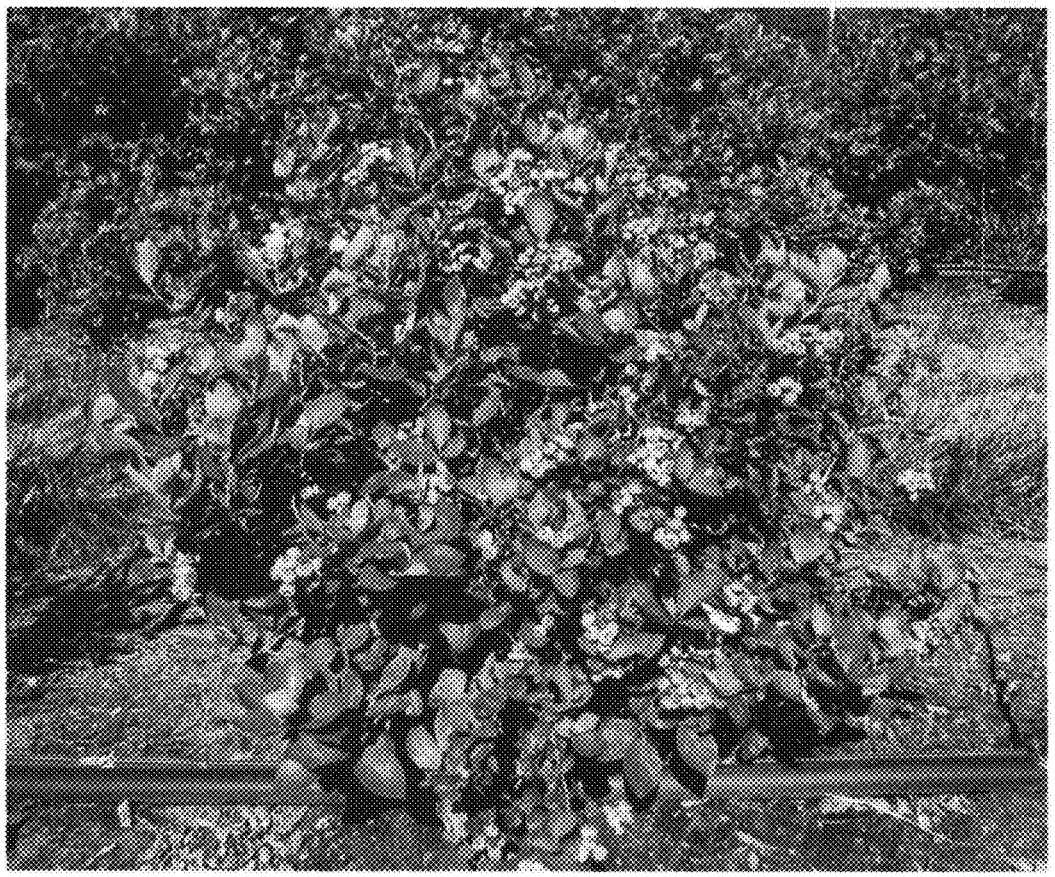
FIG. 1 is a photograph of the new variety 'ZF06-043', demonstrating the plant's compact growth habit.
Figure 2:
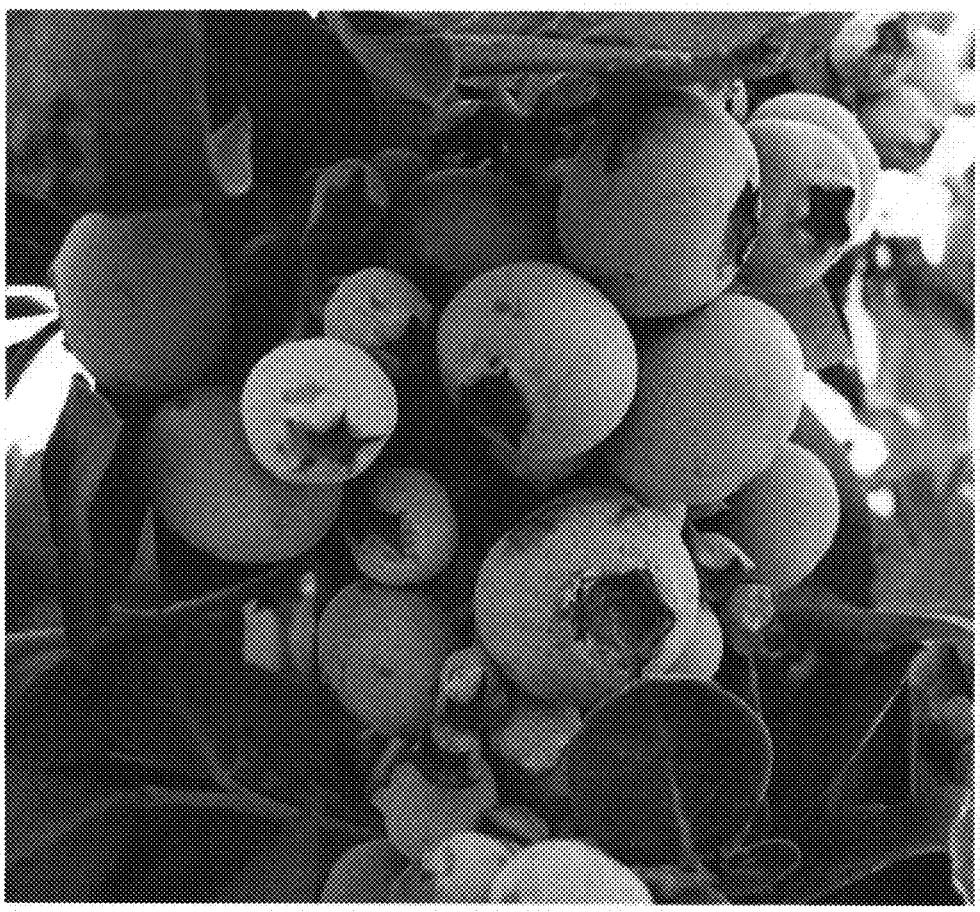
FIG. 2 is a photograph of the fruit of the new variety 'ZF06-043'.
Figure 3:
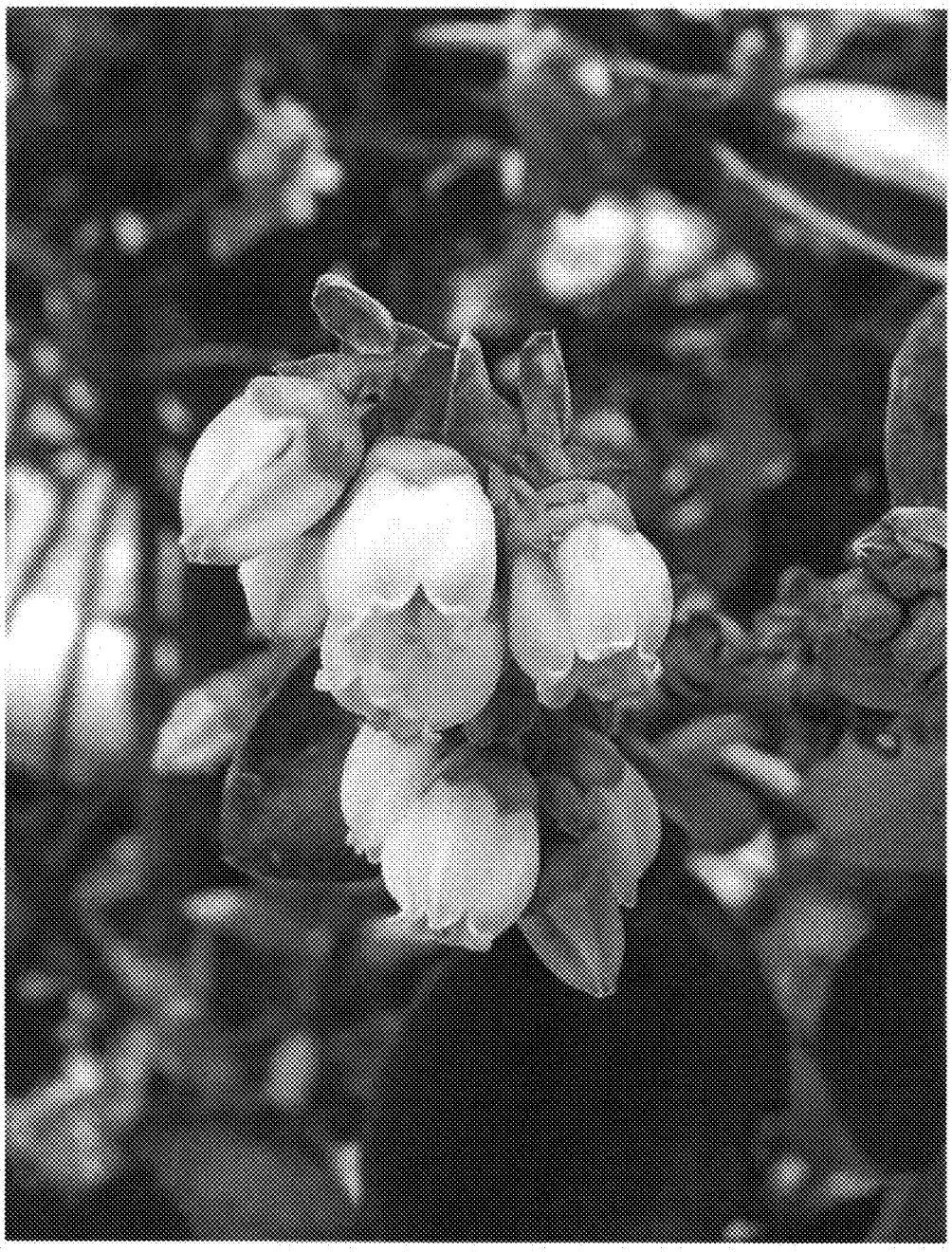
FIG. 3 is a photograph of the flowers of the new variety 'ZF06-043'.
Figure 4:
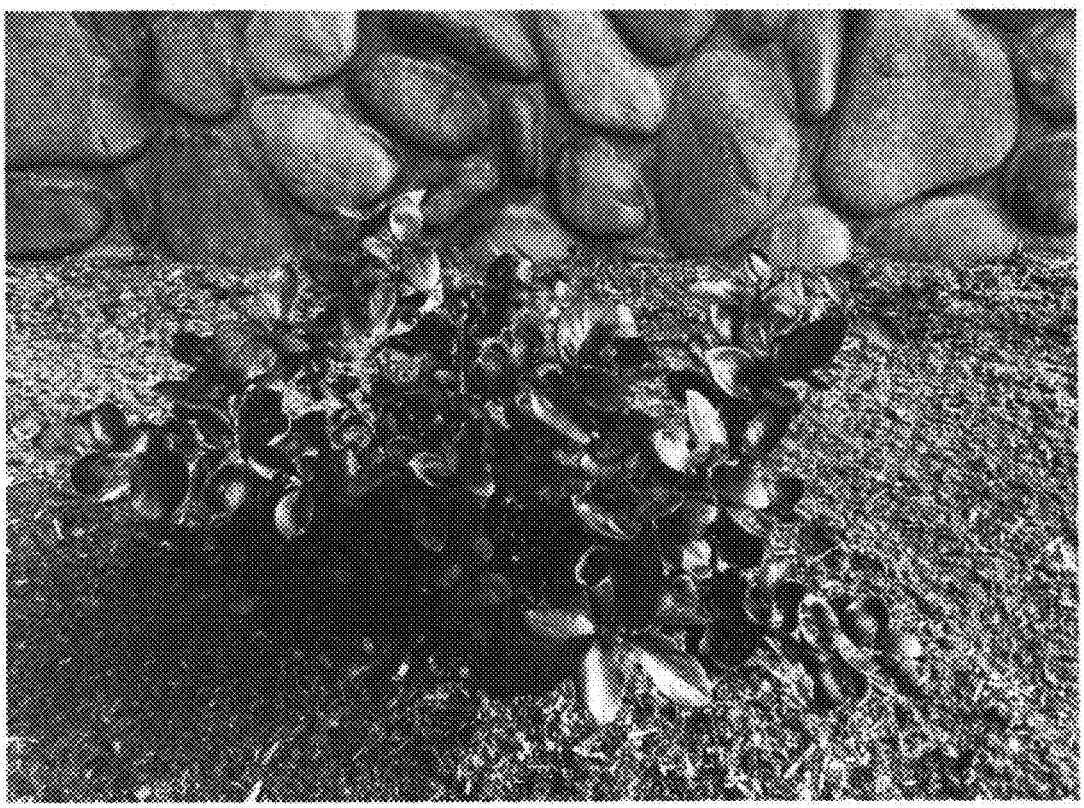
FIG. 4 is a photograph of the fall foliage of the new variety 'ZF06-043'.
Figure 5:
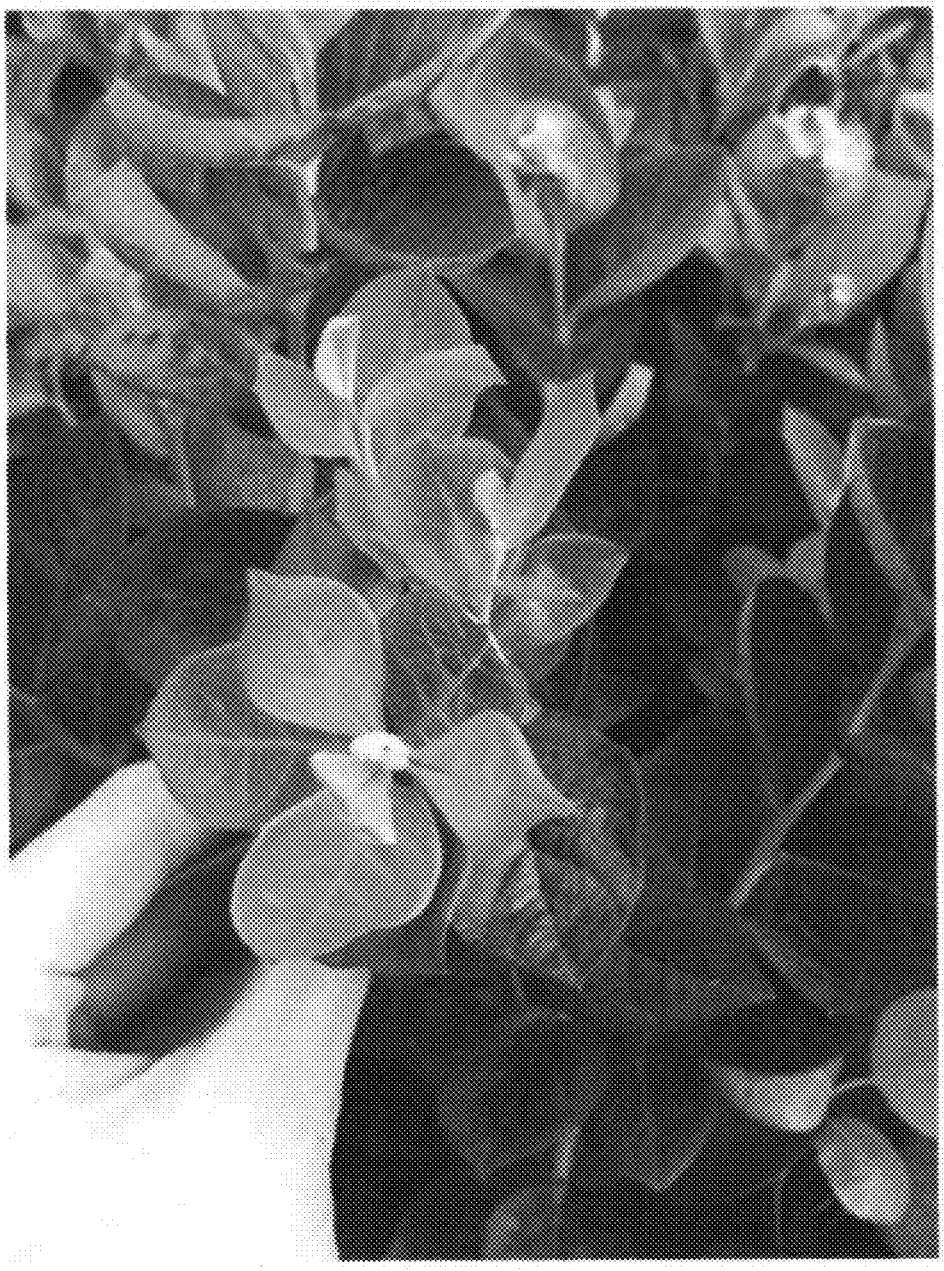
FIG. 5 is a photograph of the pink and orange new growth of the new variety 'ZF06-043'.

The following detailed description sets forth the distinctive characteristics of 'ZF06-043'. The data which define these characteristics were collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:
- *a. Family.*—Ericaceae.
- *b. Genus.*—*Vaccinium.*
- *c. Species.*—*corymbosum.*
- *d. Common name*—Highbush blueberry.

Parentage:
- *Female parent.*—FLX-2 (U.S. Plant Pat. No. 19,381).
- *Male parent.*—Toro (unpatented).

Market class: 'ZF06-043' is an ornamental blueberry variety intended for the nursery, landscape, and home gardening market.

PLANT

Plant size: Medium-sized and round.
- *a. Height of plant.*—Average of 23 inches (about 58 cm).
- *b. Canopy diameter.*—Average of 20 inches (about 51 cm).

Growth habit: Compact and round.

Plant vigor: Moderate, produces an average of 4 new canes per year.

Twigginess: Low.

Suckering: No suckering has been noted.

Evergreenness: Evergreen in Lowell, Oreg.

Chilling requirement: Approximately 500 hours of temperatures at or below 45° F. (about 7° C.).

Cold hardiness: Expected range of adaptability USDA hardiness zones 6-8.

Productivity: In Lowell, Oreg., the average per plant harvest weight on 3-year-old plants is 3 lbs (about 1.36 kg).

Propagation: Easy to propagate from softwood cuttings.

Disease resistance/susceptibility:
- *a. Phytophthora.*—Does not appear to be overly susceptible.
- *b. Stem blight.*—Does not appear to be overly susceptible.
- *c. Cane canker.*—Does not appear to be overly susceptible.
- *d. Leaf spot.*—Does not appear to be overly susceptible.
- *e. Bud mites.*—Does not appear to be overly susceptible.

Survival: Good. Plants grow and survive well in both nursery and field settings.

TRUNK AND BRANCHES

Surface texture:
- *a. Surface texture new wood.*—Smooth.
- *b. Surface texture* 1-*year wood.*—Smooth.
- *c. Surface texture* 3-*year and older wood.*—Smooth turning to rough.

Color:
- *a. Color new wood.*—Pantone Green Banana 14-0434.
- *b. Color* 1-*year wood.*—Pantone Green Banana 14-0434.
- *c. Color* 3-*year and older wood.*—Pantone Sand 15-1225 and Pantone Cocoa Brown 18-1222.

FOLIAGE

Internode length: Average of 14.6 mm.

Leaf dimensions:
- *a. Leaf length.*—Average of 44.7 mm.
- *b. Leaf width.*—Average of 27.93 mm.

Leaf shape: Elliptical, with acute apex and base.

Leaf margin: Entire.

Leaf color upper leaf surface:
- *a. New leaf color.*—Pantone Green Banana 14-0434, with tips Pantone Apricot Brandy 17-1540 and Pantone Crabapple 16-1532.
- *b. Mature leaf color.*—Pantone Cypress 18-0322.

Leaf color lower leaf surface: Pantone Sage 16-0421.

Pubescence:
- *a. Pubescence upper leaf surface.*—Absent.
- *b. Pubescence lower leaf surface.*—Absent.
- *c. Pubescence leaf margins.*—Absent.

Precocity: Flowers appear before new vegetative growth in Lowell, Oreg.

Petiole:
- *a. Petiole length.*—Average length of 3.38 mm.
- *b. Petiole color.*—Top surface Pantone Celery Green 13-0532, underside Pantone Sweet Pea 15-0531.
- *c. Petiole surface texture.*—Smooth.

FLOWERS

Flower arrangement: Arranged alternately along the distal portion of the branch.

Fragrance: Faint, sweet fragrance.

Flower shape: Urceolate.

Flower bud density: Moderate.

Flower length: Average length of 8.3 mm.

Immature flower color: Pantone Pastel Parchment 11-0603 and Pantone Bubblegum 17-1928.

Flowering cluster: Moderately loose.

Flowering period: First flowers appear in mid-April through the end of May.

Number of flowers: Average of 4-5 flowers per cluster.

Stigma location: Average of 0.5 mm beyond the lip of the corolla.

Corolla:
- *a. Corolla length.*—Average of 5.5 mm.
- *b. Corolla diameter.*—Average of 5.8 mm.
- *c. Corolla color.*—Pantone Pastel Parchment 11-0603.

*d. Corolla surface texture*.—Smooth.
*e. Corolla aperture*.—Average of 6.4 mm.

Calyx:
*a. Calyx diameter*.—Average of 4.2 mm.
*b. Calyx color*.—Pantone Spinach Green 16-0439.
*c. Calyx surface texture*.—Smooth.

Flower pedicel:
*a. Pedicel length*.—Average of 3 mm.
*b. Pedicel color*.—Pantone Spinach Green 16-0439.
*c. Pedicel surface texture*.—Smooth.

Flower peduncle:
*a. Peduncle length*.—Average of 9 mm.
*b. Peduncle color*.—Pantone Mellow Green 12-0426.
*c. Peduncle surface texture*.—Smooth.

Style length: Average of 5.7 mm.
Pistil color: Pantone Herbal Garden 15-0336.

Anther:
*a. Anther length*.—Average of 4.2 mm.
*b. Anther color*.—Pantone Red Ochre 18-1442.

Pollen:
*a. Pollen staining*.—95% fertile, staining using 2% acetocarmine stain.
*b. Pollen abundance*.—High.
*c. Pollen color*.—Pantone Mellow Yellow 12-0720.

Self compatibility: Good, 80% of self pollinated flowers reaching maturity.

FRUIT

Mean harvest date first pick: July 26.
Mean harvest date last pick: August 2.

Calyx:
*a. Calyx aperture*.—Average of 5.3 mm.
*b. Calyx lobes*.—Small.
*c. Calyx depth*.—Average of 0.69 mm.

Berry cluster: Moderately loose.
Berry pedicel length: Average of 7 mm.
Berry peduncle length: Highly variable, averaging 14.9 mm.
Berries per cluster: Average of 3-5 berries per cluster.
Berry detachment: Easy detachment force.
Berry weight: Average of 1.2 g.
Berry height: Average of 10.43 mm.
Berry width: Average of 16.1 mm.
Berry shape: Globose.

Berry color:
*a. Immature berry color*.—Pantone Green Banana 14-0434 and Pantone Crabapple 16-1532.
*b. Berry skin color on plant*.—Pantone Gray Dawn 14-4106.
*c. Berry skin color after harvest*.—Pantone Lilac Gray 14-3903.
*d. Berry skin color after polishing*.—Pantone India Ink 19-4019.

Berry wax: Medium wax, moderately persistent.
Berry flesh color: Pantone White Jade 12-0315.
Pedicel scar: Small, dry scar, averaging 1.5 mm in diameter.
Berry firmness: Moderately firm.
Berry flavor: Mildly sweet.
Berry texture: Smooth.
Seeds per berry: Average of 26 seeds per fruit.

SEEDS

Seed color: Pantone Carnelian 16-1435.
Seed length: Average of 1.54 mm.
Seed width: Average of 1.08 mm.
Seed weight: Average of 0.5 mg.

The invention claimed is:

1. A new and distinct variety of blueberry plant named ‘ZF06-043’, substantially as illustrated and described herein.

* * * * *